(12) United States Patent
Green et al.

(10) Patent No.: US 9,549,761 B2
(45) Date of Patent: Jan. 24, 2017

(54) ENDOSCOPIC FOREIGN BODY RETRIEVAL

(75) Inventors: Alex Green, Columbus, OH (US); Brendan Boyle, Columbus, OH (US)

(73) Assignee: Research Institute At Nationwide Children's Hospital, Columbus, OH (US)

( * ) Notice: Subject to any disclaimer, the term of this patent is extended or adjusted under 35 U.S.C. 154(b) by 220 days.

(21) Appl. No.: 14/126,903

(22) PCT Filed: Jun. 15, 2012

(86) PCT No.: PCT/US2012/042748
§ 371 (c)(1),
(2), (4) Date: Feb. 21, 2014

(87) PCT Pub. No.: WO2012/174431
PCT Pub. Date: Dec. 20, 2012

(65) Prior Publication Data
US 2014/0213847 A1    Jul. 31, 2014

Related U.S. Application Data

(60) Provisional application No. 61/498,028, filed on Jun. 17, 2011.

(51) Int. Cl.
*A61B 1/00* (2006.01)
*A61B 17/50* (2006.01)
(Continued)

(52) U.S. Cl.
CPC .............. *A61B 17/50* (2013.01); *A61B 1/018* (2013.01); *A61B 17/00234* (2013.01);
(Continued)

(58) Field of Classification Search
CPC ............ A61B 1/00085; A61B 1/00087; A61B 1/00089; A61B 1/00101
(Continued)

(56) References Cited

U.S. PATENT DOCUMENTS 7,507,200 B2    3/2009  Okada
2003/0009085 A1  1/2003  Arai et al.
(Continued)

OTHER PUBLICATIONS

International Search Report and Written Opinion for International Application No. PCDT/US2012/042748, date of mailing Sep. 12, 2012.

*Primary Examiner* — Timothy J Neal
(74) *Attorney, Agent, or Firm* — Christopher Paradies; Paradies Law P.A.

(57) ABSTRACT

The present application discloses endoscopy systems and devices for use therewith, wherein such systems and devices are designed for use in foreign body retrieval procedures. Moreover, the present application discloses methods of retrieving foreign bodies using the provided systems and devices. In one exemplary embodiment, a foreign body retrieval device capable for use with an endoscope is provided. The retrieval device comprises a housing and a capture tool disposed within and movable relative to the housing. The housing has a proximal end, a distal end, and at least one cavity. The proximal end of the housing is configured for attachment to the distal end of an endoscope and the distal end comprises an opening for at least partially receiving a foreign body in the at least one cavity. The capture tool defines an at least partially closeable aperture.

19 Claims, 12 Drawing Sheets

(51) Int. Cl.
  *A61B 17/00* (2006.01)
  *A61B 17/22* (2006.01)
  *A61B 17/29* (2006.01)
  *A61B 1/018* (2006.01)
  *A61B 1/04* (2006.01)

(52) U.S. Cl.
  CPC ........ *A61B 17/22031* (2013.01); *A61B 17/29* (2013.01); *A61B 2017/00358* (2013.01); *A61B 2017/22035* (2013.01); *A61B 2217/005* (2013.01)

(58) Field of Classification Search
  USPC .................................. 600/104, 121, 123, 129
  See application file for complete search history.

(56) References Cited

U.S. PATENT DOCUMENTS

| | | | |
|---|---|---|---|
| 2004/0158127 A1 | 8/2004 | Okada | |
| 2008/0103508 A1* | 5/2008 | Karakurum | ...... A61B 17/00234 606/127 |

\* cited by examiner

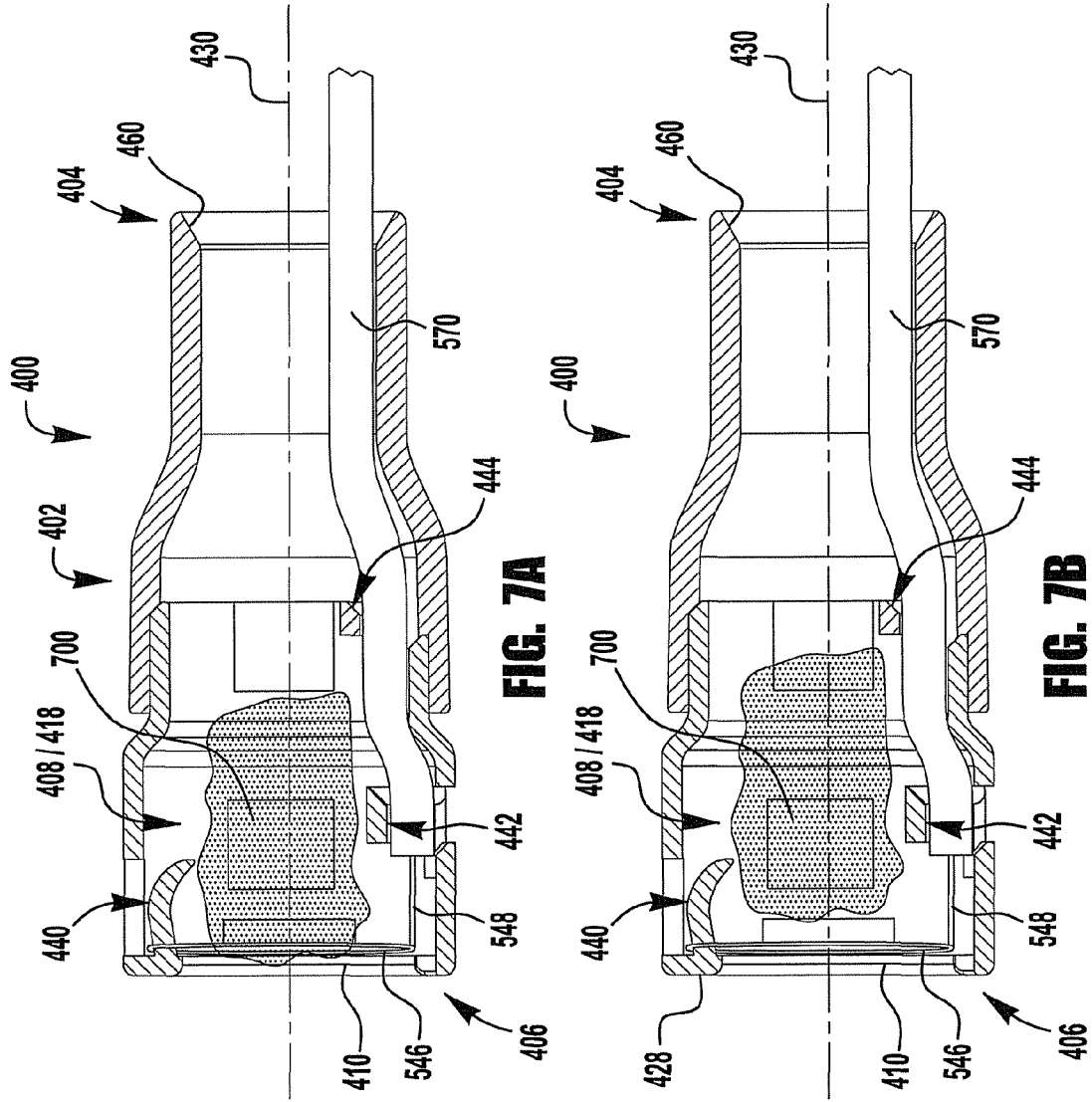

ENDOSCOPIC FOREIGN BODY RETRIEVAL

CROSS REFERENCE TO RELATED APPLICATION

This application is the U.S. national stage entry of PCT/US2012/042748, with an international filing date of Jun. 15, 2012, which claims priority to and any other benefit of U.S. Provisional Patent Application Ser. No. 61/498,028, filed Jun. 17, 2011 and titled "Endoscopic Foreign Body Retrieval", the entire contents of both applications are hereby incorporated by reference in its entirety.

FIELD OF THE INVENTION

The present application relates to endoscopy systems, and devices for use therewith, that may be used for foreign body retrieval procedures. The present application also relates to foreign body retrieval methods using the provided systems and devices.

BACKGROUND

Endoscopy is a medical procedure that provides a clinician access to anatomical structures (e.g., the esophagus, gastrointestinal tract, pelvic cavity, or respiratory tract) in a minimally invasive manner for visual inspection, imaging, biopsy, manipulation, or other diagnostic or surgical purposes. A variety of different endoscope designs have been developed and adapted for use in the context of accessing particular anatomical structures, such as the gastrointestinal tract (e.g., colonoscopes, gastroscopes, and sigmoidoscopes), the respiratory tract (e.g., rhinoscopes and bronchoscopes), the abdominal or pelvic cavity (e.g., laparascopes), and the reproductive system (e.g., hysteroscopes and falloscopes).

Many types of endoscopes are known and they typically comprise a rigid or flexible body, an illumination means (e.g., light or light delivery system), an imaging means (e.g. lens system or camera), and one or more distally-positioned medical tools (e.g., biopsy forceps, injection needles, haemostatic clips, electrosurgical snares, grasping baskets, retrieval nets, and suction tips), all of which are in communication with equipment that controls their respective functions.

Endoscopic foreign body retrieval is a frequently required procedure in both adult and pediatric gastroenterology and pulmonology, and there are numerous approaches to retrieval. A foreign body may be any ingested object, such as, for example, a food bolus, coin, button, tooth, fish bone, battery, etc. The method selected by a clinician to retrieve a foreign body often depends upon a variety of factors, including but not limited to, the specific patient, the foreign body, the anatomical structure(s) involved, the available equipment, and the clinician's personal experience and preference. Typically, the procedure involves multiple attempts to grasp the foreign body using an endoscope with distally-positioned retrieval nets, forceps, or other grasping device. Although such devices have been used for foreign body retrieval procedures, they are not designed for such use and therefore have numerous limitations, including but not limited to, high cost, limited visibility, patient tissue injury and/or discomfort, prolonged procedure time and cost, and failure to retrieve the foreign body.

Such devices and procedures are also unsuitable for emergency removal of a foreign body, such as from an esophagus, bronchus, or proximal gastrointestinal tract. One observed example of such deficiency is that a conventional retrieval net is sometimes unable to grasp or surround an entire foreign body or bypass beyond a foreign body. In part, this is due to the orientation and malleable nature of a conventional net's support wires. Another observed example of such deficiency is that conventional forceps are prone to difficulty in obtaining and maintaining control of a foreign body. Similarly, conventional snare devices have been observed to have difficulty in grasping a foreign body without causing it to break apart. Due to the deficiencies of such conventional devices, multiple attempts to remove a foreign body are often required, which can lead to, among other difficulties, prolonged procedure times and increased incidence of tissue trauma.

Instead of such devices and procedures, or if such devices and procedures do not successfully retrieve a foreign body, an endoscope with a distally-positioned banding and suction device, such as the SpeedBand SuperView Super 7™ Multiple Band Ligator (Boston Scientific, Natick, Mass.), may be employed. However, even these devices have their limitations, such as poor distal visibility, no mechanism of securing a suctioned foreign body, instrument expense, and inability to retrieve larger foreign bodies.

SUMMARY

The present application discloses endoscopy systems and devices for use therewith, wherein such systems and devices are designed for use in foreign body retrieval procedures. Moreover, the present application discloses methods of retrieving foreign bodies using the provided systems and devices.

In one exemplary embodiment, a foreign body retrieval device capable for use with an endoscope is provided. The retrieval device comprises a housing and a capture tool disposed within and movable relative to the housing. The housing has a proximal end, a distal end, and at least one cavity. The proximal end of the housing is configured for attachment to the distal end of an endoscope and the distal end comprises an opening for at least partially receiving a foreign body in the at least one cavity. The capture tool defines an at least partially closeable aperture.

In another exemplary embodiment, a foreign body retrieval system is provided. The foreign body retrieval system comprises an endoscope having a distal end for insertion into a patient and a retrieval device attached to the distal end of the endoscope. The retrieval device comprises a housing and a capture tool. The housing has at least one cavity and an opening for at least partially receiving a foreign body. The capture tool is at least partially disposed within and movable relative to the housing and defines an at least partially closeable aperture.

In yet another exemplary embodiment, a method of retrieving a foreign body from the esophagus of a patient is provided. The method comprises the step of inserting a distal end of an endoscope into a patient's mouth. A retrieval device is attached to the distal end of the endoscope. The retrieval device comprises a housing and a capture tool. The housing has at least one cavity and an opening for at least partially receiving a foreign body. The capture tool is disposed within and movable relative to the housing and defines an at least partially closeable aperture. The distal end of the endoscope and the retrieval device are advanced through the esophagus of the patient. At least a portion of a foreign body is received in the at least one cavity of the housing. The capture tool is moved relative to the housing to at least partially close the aperture defined by the capture tool. The distal end of the endoscope and the retrieval device are removed from the patient to retrieve the foreign body.

These and additional embodiments will become apparent in the course of the following detailed description.

BRIEF DESCRIPTION OF THE DRAWINGS

A more complete appreciation of the invention and the many embodiments thereof will be readily obtained as the same becomes better understood by reference to the following detailed description when considered in connection with the accompanying drawings, wherein:

FIGS. 7A and 7B are partial side cross sectional views of the retrieval device of FIG. 5B, wherein a foreign body is at least partially received in a cavity of the retrieval device.

DESCRIPTION OF EMBODIMENTS

Figure 1:
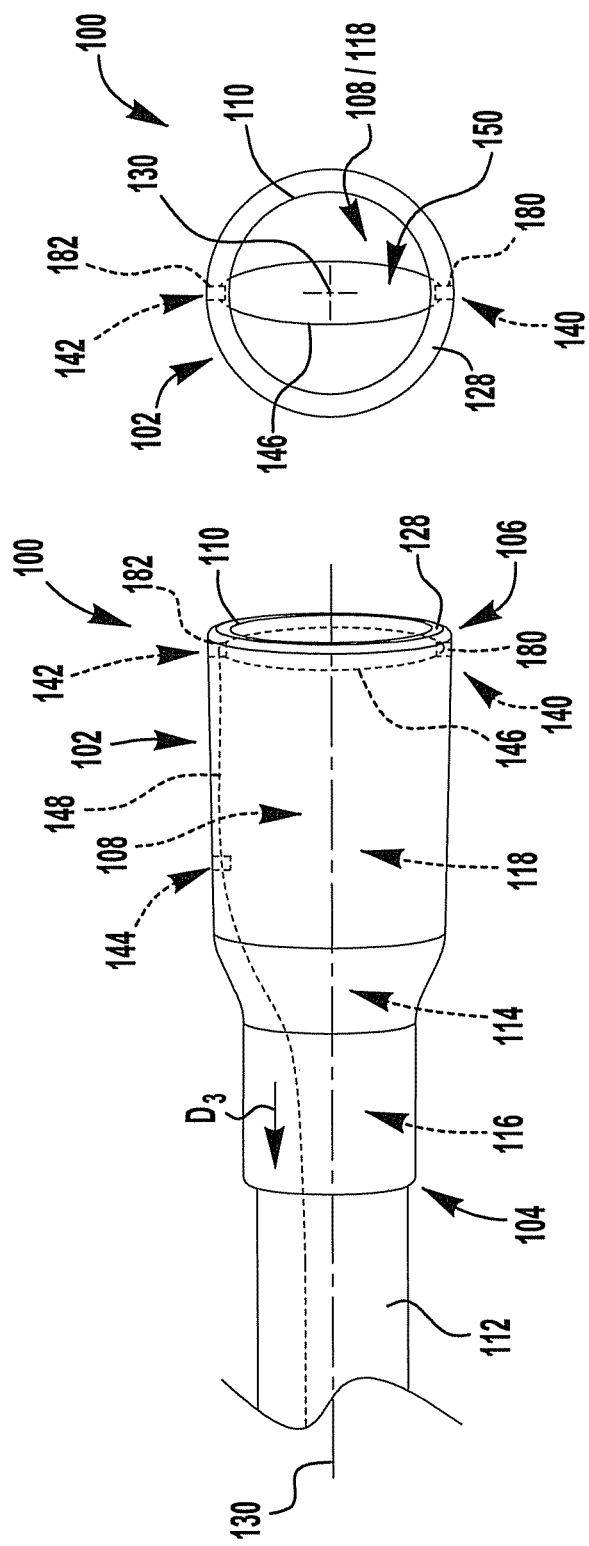
FIG. 1 illustrates a side view and an end view of a retrieval device according to an embodiment of the present application.

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Endoscopy systems, devices, and procedures relating to esophageal foreign body retrieval are discussed with particularity herein to illustrate embodiments of the present invention. However, it is contemplated that the invention is applicable to systems, devices, and procedures relating to retrieval of foreign bodies from other anatomical structures, such as, for example, the bronchus, colon, or proximal gastrointestinal tract. Accordingly, nothing herein shall be construed as limiting the invention to systems, devices, and procedures for esophageal foreign body retrieval.

The foreign body retrieval systems of the present application generally include an endoscope or endoscopy system having a distally attached retrieval device or are otherwise configured for use with, intended for attachment with or suitable for use with an endoscope or endoscopy system. As will become apparent to those reviewing this application in detail, the particular configuration of the endoscope or endoscopy system utilized or otherwise associated with the retrieval device is not particularly limited. The retrieval devices of the present application include a housing and at least one movable capture tool. The provided retrieval systems and devices offer one or more advantages over systems and devices typically used for foreign body retrieval, including, but not limited to, reduced cost, improved visibility, reduced patient tissue injury and/or discomfort, reduced procedure time and cost, and reduction in failures to retrieve foreign bodies.

The retrieval devices of the present application comprise a housing having a proximal end, a distal end, and at least one cavity. The proximal end is configured for attachment to the distal end of the endoscope or endoscopy system. The distal end comprises an opening for at least partially receiving a foreign body in the at least one cavity of the housing.

For example, the retrieval devices illustrated in FIGS. 1-3 and 8A-9B each comprise a housing 102 having a proximal end 104, a distal end 106, and a cavity 108. The proximal end 104 is attached to the distal end of an endoscope 112 and the distal end 106 comprises an opening 110 for at least partially receiving a foreign body in the cavity 108 of the housing 102. Further, the housing 102 defines a passage 114 extending from the proximal end 104 to the distal end 106 along a longitudinal axis 130 of the housing 102. At least a portion of the passage communicates with, or is accessible to, one or more channels of the endoscope 112 (e.g., an auxiliary channel and/or working channel of an endoscope). A first portion 116 of the passage 114 is configured for attachment to the distal end of the endoscope 112 and a second portion 118 of the passage defines the cavity 108.

Further, the retrieval device 400 illustrated in FIGS. 4A-7B comprises housing 402 having a proximal end 404, a distal end 406, and a cavity 408. The proximal end 404 is attached to the distal end of an endoscope 510 (FIG. 5A) and the distal end 406 comprises an opening 410 for at least partially receiving a foreign body in the cavity 408 of the housing 402. Further, the housing 402 defines a passage 414 extending from the proximal end 404 to the distal end 406 along a longitudinal axis 430 of the housing 402. At least a portion of the passage communicates with, or is accessible to, one or more channels of the endoscope 510 (e.g., an auxiliary channel and/or working channel of an endoscope). A first portion 416 of the passage 414 is configured for attachment to the distal end of the endoscope 510 and a second portion 418 of the passage defines the cavity 408.

As illustrated in the Figures, the diameter of the first portion 116, 416 of the passage 114, 414 is less than the diameter of the second portion 118, 418 of the passage for the retrieval device housings 102, 402. For example, as shown in FIG. 4D, the diameter $D_1$ of the first portion 416 of the passage 414 is less than the diameter $D_2$ of the second portion 418 of the passage. However, in certain embodiments, the diameter of the first portion of the passage may be greater than or equal to the diameter of the second portion of the passage. Further, the transition between the first and second portions of the passage may be continuous, graduated, and/or tapered. The first and second portions of the passage may also be at least partially separated by a membrane or other material.

In certain embodiments, the retrieval device housings of the present application are designed to be of dimensions suitable for insertion into and operation within the esophagus and for capture and retrieval of foreign bodies typically encountered within the esophagus. Further, the retrieval device housings generally comprise a smooth outer surface to facilitate insertion into and operation within the esophagus or other anatomical structure.

For example, the overall length of the housing from the proximal end to the distal end may be from about 0.5 to about 2.0 inches. Accordingly, the overall length of the housing may be from about 0.5-0.6, 0.6-0.7, 0.7-0.8, 0.8-0.9, 0.9-1.0, 1.0-1.1, 1.1-1.2, 1.2-1.3, 1.3-1.4, 1.4-1.5, 1.5-1.6, 1.6-1.7, 1.7-1.8, 1.8-1.9, 1.0-2.0 inches, and combinations thereof. As an example, in one embodiment of the retrieval device 400 shown in FIG. 4D, the length $L_1$ of the first portion 416 of the passage 414 (including the transition between the first portion 416 and second portion 418) is between about 0.7 and 0.9 inch, or about 0.78 inch, and the length $L_2$ of the second portion 418 of the passage is between about 0.8 and 1.0 inch, or about 0.94 inch, such that the overall length of the housing 402 from the proximal end 404 to the distal end 406 is between about 1.5 and 1.9 inches, or about 1.72 inches. It should be understood that the respective lengths of the first portion and second portion of the passage may vary depending on the particular embodiment or application. For example, in certain embodiments, the length of the portion of the housing configured for attachment to the distal end of the endoscope may be between about 0.1 and 1.0 inch and the length of the portion of the housing defining the receiving cavity may be between about 0.7 and 1.5 inches.

Further, the diameter of the second portion of the passage defining the cavity for receiving a foreign body may be from about 0.5 to about 1.8 inches. Accordingly, the diameter of the second portion of the passage may be from about 0.5-0.6, 0.6-0.7, 0.7-0.8; 0.8-0.9, 0.9-1.0, 1.0-1.1, 1.1-1.2, 1.2-1.3, 1.3-1.4, 1.4-1.5, 1.5-1.6, 1.6-1.7, 1.7-1.8 inches, and combinations thereof. As an example, in one embodiment of the retrieval device 400 shown in FIG. 4D, the diameter $D_2$ of the second portion 418 of the passage 414 defining the cavity 408 for receiving a foreign body is between about 0.5 and 0.8 inch, or about 0.66 inch, or about ⅝ inch.

The housing of the retrieval device may be attached to the endoscope or endoscopy system in a variety of ways. As illustrated in the Figures, at least a portion of the proximal end 104, 404 of the housings 102, 402 are configured to slide over at least a portion of the distal end of an endoscope to attach the retrieval device 100, 400 to the endoscope. For example, as shown in FIG. 5A, the proximal end 404 of the housing 402 is configured to slide over a distal portion of the endoscope 510. As such, the distal end of the endoscope 510 is received in the first portion 416 of the passage 414. The proximal end 104, 404 of the housings 102, 402 may also be configured to facilitate insertion of the endoscope into the first portion 116, 416 of the passage 114, 414. For example, as shown in FIGS. 4D, 5B, and 7A-7B, the proximal end 404 of the housing 402 comprises a tapered opening 460 to facilitate insertion of the distal end of the endoscope 510 into the first portion 416 of the passage 414.

Attachment of the retrieval device to the endoscope or endoscopy system may be removable or substantially permanent. For example, in some embodiments, the proximal end of the housing and/or the first portion of the passage may be permanently attached to the endoscope, such as, for example, with a medically-suitable glue, adhesive, weld, or fastening device. In other embodiments, however, the proximal end of the housing and/or the first portion of the passage may be removably attached to the endoscope, such as, for example, with a medical tape, elastomeric bands, clips, snap fitting, compression fitting, or other fastening device that permits removal of the housing from the endoscope. As an additional example, removable attachment may be achieved using a friction fit or through tension created by one or both of the selected dimensions of the housing or the selected resiliency of the material of construction of the housing.

The retrieval devices of the present application may be used with a variety of endoscopes or endoscopy systems. For example, in certain embodiments, the proximal end and/or first portion of the passage may have a diameter suitable for attaching the retrieval device to a conventional endoscope and/or gastroscope. In these embodiments, the diameter of the proximal end and/or first portion of the passage may be from about 5.9 mm to about 12.9 mm. Accordingly, the diameter may be from about 5.9-6.1 mm, 6.1-6.3 mm, 6.3 -6.5 mm, 6.5-6.7 mm, 6.7-6.9 mm, 6.9-7.1 mm, 7.1-7.3 mm, 7.3-7.5 mm, 7.5-7.7 mm, 7.7-7.9 mm, 7.9-8.1 mm, 8.1-8.3 mm, 8.3-8.5 mm, 8.5-8.7 mm, 8.7-8.9 mm, 8.9-9.1 mm, 9.1-9.3 mm, 9.3-9.5 mm, 9.5-9.7 mm, 9.7-9.9 mm, 9.9-10.1 mm, 10.1-10.3 mm, 10.3-10.5 mm, 10.5-10.7 mm, 10.7-10.9 mm, 10.9-11.1 mm, 11.1-11.3 mm, 11.3-11.5 mm, 11.5-11.7 mm, 11.7-11.9 mm, 11.9-12.1 mm, 12.1-12.3 mm, 12.3-12.5 mm, 12.5-12.7 mm, 12.7-12.9 mm, and combinations thereof. As an example, in one embodiment of the retrieval device 400 shown in FIG. 4D, the diameter $D_1$ of the proximal end 404 or the first portion 416 of the passage 414 is between about 0.3 and 0.5 inch, or about 0.39 inch, or about 25/64 inch.

Further, in certain embodiments, the proximal end and/or first portion of the passage may have a diameter suitable for attaching the retrieval device to a conventional colonoscope. In these embodiments, the diameter of the proximal end and/or first portion of the passage may be from about 11.5 mm to about 13.7 mm. Accordingly, the diameter may be from about 11.5-11.7 mm, 11.7-11.9 mm, 11.9-12.1 mm, 12.1-12.3 mm, 12.3-12.5 mm, 12.5-12.7 mm, 12.7-12.9 mm, 12.9-13.1 mm, 13.1-13.3 mm, 13.3-13.5 mm, 13.5-13.7 mm, and combinations thereof. In other certain embodiments, the proximal end and/or first portion of the passage may have a diameter suitable for attaching the retrieval device to a conventional bronchoscope. In these embodiments, the diameter of the proximal end and/or first portion of the passage may be from about 2.8 mm to about 6.3 mm. Accordingly, the diameter may be from about 2.8-3.0 mm, 3.0-3.2 mm, 3.2-3.4 mm, 3.4-3.6 mm, 3.6-3.8 mm, 3.8-4.0 mm, 4.0-4.2 mm, 4.2-4.4 mm, 4.4-4.6 mm, 4.6-4.8 mm, 4.8-5.0 mm, 5.0-5.2 mm, 5.2-5.4 mm, 5.4-5.6 mm, 5.6-5.8 mm, 5.8-6.0 mm, 6.0-6.3 mm, and combinations thereof.

The retrieval device cavity adapted to receive at least a portion of the foreign body or the second portion of the passage defining the receiving cavity may be configured in a variety of ways. For example, the receiving cavity may be zoned or segmented to form a plurality of receiving cavities. Further, the receiving cavity may comprise one or more features that facilitate use of the capture tool. For example, the housing may comprise one or more openings for accessing a capture tool disposed within the housing or receiving cavity of the retrieval device. The interior of the receiving cavity may also comprise one or more features, such as channels or spaces, that facilitate movement of a capture tool disposed within the housing or receiving cavity.

Further, at least a portion of the receiving cavity may be non-symmetrically formed within the housing. For example, the receiving cavity may be configured such that at least a portion of the capture tool does not block or obstruct the cavity opening at the distal end of the housing when the capture tool is in a first position, such as, for example, when the capture tool is at rest or not actuated by a clinician. As illustrated in the Figures, at least a portion of the cavity opening 110, 410 of the housings 102, 402 has a diameter that is less than the diameter of the second portion 118, 418 of the passage 114, 414. As such, the distal end 106, 406 of the housing 102, 402 comprises a flanged portion 128, 428 between the outer surface of the housing and the cavity opening 110, 410. At least a portion of the capture tool may be disposed in the space created within the receiving cavity 108, 408 behind the flanged portion 128, 428. As an example, in one embodiment, the difference between the diameter of the cavity opening and the diameter of the second portion of the passage is about ⅛ inch. The flanged portion may or may not extend about the entire circumference of the cavity opening. Further, the flanged portion may be incongruent and the length and/or thickness of the flanged portion may vary about the circumference of the cavity opening. In certain embodiments, however, the retrieval device housing may not comprise a flanged portion and/or the diameter of the cavity opening may be substantially the same as the diameter of the receiving cavity.

The housing of the retrieval device may be a single structure or comprise one or more components integrally formed or otherwise secured together. For example, as illustrated in FIGS. 4A-7B, the housing 402 comprises a first part 470 attached to a second part 472 to form the housing. As shown in FIG. 4D, the second part 472 comprises an end portion 474 that is configured to be received in a corresponding end portion 476 of the first part 470. Attachment between the first part 470 and the second part 472 may be substantially permanent or removable and by any one or more of the methods described herein. In certain embodiments, having the housing formed of multiple components configured to be attached together facilitates assembly and use of the retrieval device. For example, the capture tool may be placed within and/or attached to the interior of a first housing component separate from attachment of a second housing component to the endoscope. The first housing component may then be attached to the second housing component to form the retrieval device.

The housing may be constructed using a variety of materials. In certain embodiments, the housing may be constructed of a polymeric material or alternatively may be constructed of a metallic material. For example, at least a portion of the housing may be constructed of a transparent material that permits observation of the foreign body to be retrieved, the surrounding anatomical structure(s), or combinations thereof. The housing may also be constructed of one or more rigid, semi-rigid, or semi-flexible materials, or combinations thereof. For example, the housing may comprise a rigid transparent silicone material. As another example, the housing may comprise a transparent plastic, such as polyethylene terephthalate (PET). One of skill in the art will appreciate that numerous transparent materials suitable for medical use are known and could be used with the provided devices and systems.

Further, one or more portions of the housing may be disposable. For example, in certain embodiments, the entire housing of the retrieval device is removed from the endoscope and disposed of after use. In other embodiments, only a portion of the housing (e.g., the second part 472 of the housing 402) is removed from another portion of the housing and disposed of after use. In some embodiments, however, one or more portions of the housing comprise a material that is capable of sterilization such that the device may be reused.

The retrieval devices of the present application comprise a capture tool disposed within the housing and movable relative to the housing. The capture tool defines an at least partially closeable aperture. In certain embodiments, the at least partially closeable aperture is completely defined by the capture tool. In other embodiments, the capture tool and the housing define the at least partially closeable aperture. The capture tool is configured such that it may be moved to at least partially block or obstruct the opening in the distal end of the housing. Further, the capture tool is configured to hold or grasp at least a portion of a foreign body that is at least partially received in the cavity of the housing.

The retrieval devices of the present application may comprise a capture tool formed as a snare or loop that is remotely manipulated by a clinician to capture, block, or otherwise secure a foreign body within at least a portion of the housing. The snare may comprise one or more elongated members that define an at least partially closable loop. The elongated member may be, for example, wire, twine, filament, cable, fiber, or other medically suitable material. Further, the at least partially closeable loop may take a variety of forms, such as, for example, oval, hexagonal, circular, or crescent shaped loops. In certain embodiments, the capture tool is capable of being extended at least partially through the end of the housing in order to capture or otherwise secure a foreign body and then retract to secure the foreign body at least partially within the housing.

FIG. 1 illustrates one possible embodiment where the retrieval device has a snare disposed within the cavity of the housing and movable relative to the housing. As illustrated in FIG. 1, the snare of retrieval device 100 comprises a loop 146 that defines an at least partially closeable aperture 150. The at least partially closeable aperture 150 is completely defined by the snare. The snare also comprises an actuation member 148 operatively attached or integral with the loop 146 of the snare. The actuation member 148 functions to allow the clinician or operator to manipulate the loop 146 of the snare. In certain embodiments, the actuation member 148 extends through the passage 114 of the housing 102 and is movably connected to the distal end of the endoscope 112.

The snare of the retrieval device 100 is movably attached to the housing 102 at a first attachment point 140 and a second attachment point 142. As illustrated in FIG. 1, the first and second attachment points 140, 142 are diametrically opposed and located on the interior of the second portion 118 of the passage 114 adjacent the distal end 106 of the housing 102. The loop 146 defining the at least partially closeable aperture 150 is formed between the first and second attachment points 140, 142. Moving the snare relative to the second attachment point 142 at least partially closes the loop 146 formed between the first and second attachment points 140, 142. The snare is configured such that it may be moved to at least partially block or obstruct the opening 110 in the distal end 106 of the housing 102. Further, the snare is configured to hold or grasp at least a portion of a foreign body that is at least partially received in the cavity 108 of the housing 102. It is contemplated that, in certain embodiments, the attachment points may be located on a flanged portion of the housing, on the exterior of the housing, or at different locations within the housing.

The attachment points generally comprise one or more attachment members extending from or disposed within the housing of the retrieval device. For example, an attachment member may comprise an eyelet, loop, hook, one or more openings, clip, or other device or fastener that attaches the snare to the housing while allowing for movement of the snare such as to extend and capture the foreign body. As illustrated in FIG. 1, the first and second attachment points 140, 142 comprise first and second attachment members 180, 182, respectively, extending from the interior of the housing 102. In one embodiment, the first and second attachment members 180, 182 are loops or eyelets extending from the interior of the housing 102.

Moving the snare of the retrieval device 100 relative to or through the second attachment member 182 at least partially closes the loop 146. The movement of the snare relative to or through the second attachment member 182 may comprise, for example, moving one or more elongated members of the snare through a loop, eyelet, or opening in the housing 102. In certain embodiments, the snare comprises a single elongated member having an end portion formed as the loop 146. In such embodiments, the distal portion of the loop 146 is attached to the first attachment member 180 and the elongated member is movably attached to the second attachment member 182. In these embodiments, the loop 146 is at least partially closed as the elongated member is moved relative to or through the second attachment member 182. In other embodiments, the snare comprises a plurality of elongated members (e.g., two elongated members) that are configured to form the loop 146 between the first and second attachment members 180, 182. As an example, the ends of the elongated members may be attached to the first attachment member(s) 180 and the elongated members may be movably attached to the second attachment member(s) 182. In these embodiments, the loop 146 is at least partially closed as the elongated members are moved relative to or through the second attachment member(s) 182.

Figure 2C:
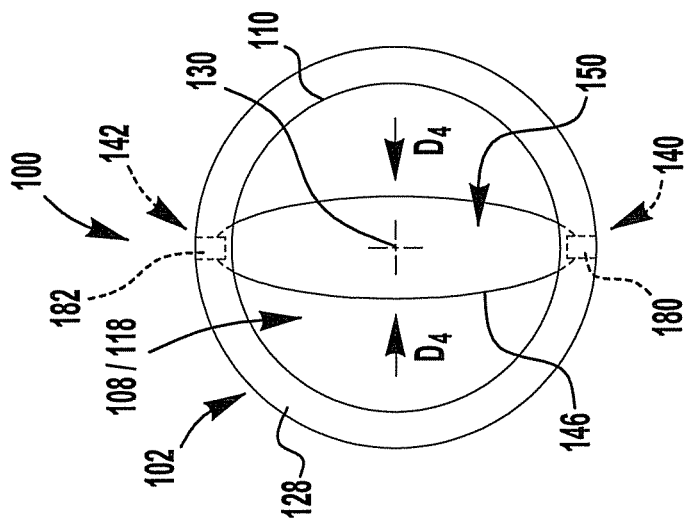
FIGS. 2A-2C illustrate end views of the retrieval device of FIG. 1 showing movement of a capture tool according to an embodiment of the present application.
Figure 2B:
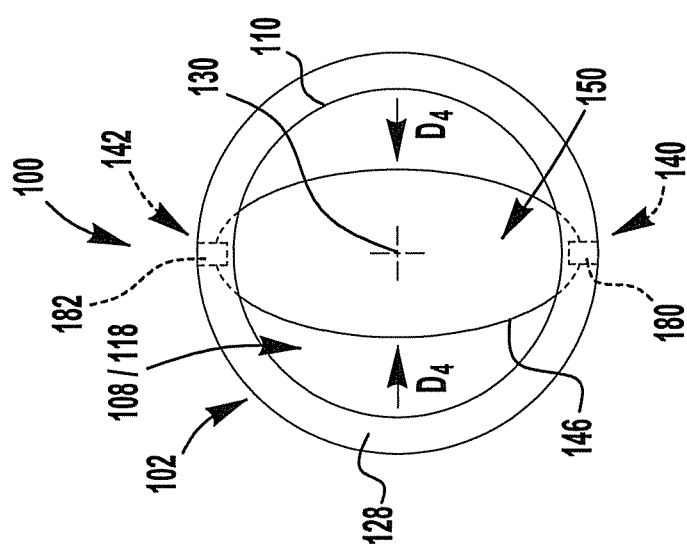
Figure 2A:
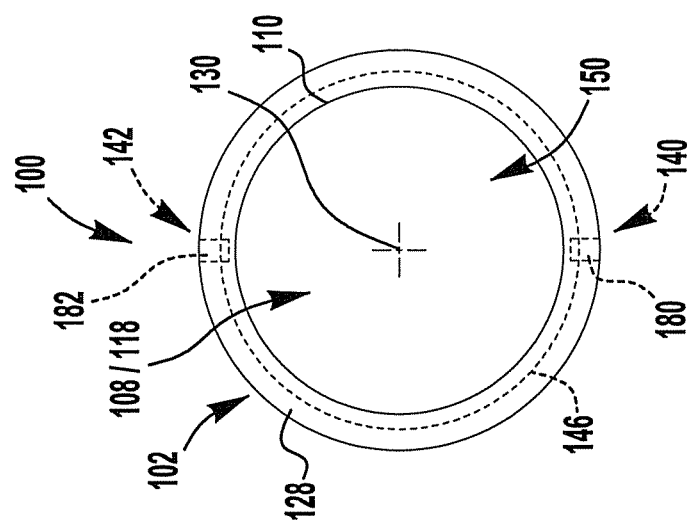

FIGS. 2A-2C are end views of the retrieval device 100 shown in FIG. 1 illustrating the movement of the loop 146 as the snare is moved relative to or through the second attachment member 182. FIG. 2A illustrates the snare in a first position, such as, for example, when the snare is at rest or not actuated by a clinician. As shown, the loop 146 of the snare is disposed within the housing 102 in the space behind the flanged portion 128 of the housing. As such, the loop 146 does not block or obstruct the cavity opening 110 at the distal end 106 of the housing 102. In the first position, the at least partially closeable aperture 150 defined by the loop 146 is larger than the cavity opening 110 such that the opening is not obstructed.

FIGS. 2B and 2C illustrate the snare in a second position, wherein the loop 146 of the snare is at least partially closed. As the snare is moved relative to or through the second attachment member 182, the elongated member(s) forming the loop 146 is moved in a direction $D_4$ toward the longitudinal axis 130 of the housing 102 or center of the cavity 108 to tighten or at least partially close the loop. Further, the aperture 150 defined by the loop 146 is at least partially closed as the snare is moved relative to the second attachment member 182. In the second position, the loop 146 of the snare at least partially blocks or obstructs the opening 110 in the distal end 106 of the housing 102. Further, the loop 146 of the snare may hold or grasp at least a portion of a foreign body that is at least partially received in the loop or the at least partially closeable aperture 150 defined by the loop.

It is contemplated that a clinician or operator may manipulate movement of the snare relative to or through the second attachment member 182 by remotely moving the actuation member 148 of the snare. For example, a clinician or operator may move the actuation member 148 manually, such as by pulling, twisting, or pushing the actuation member or one or more members operatively connected to the actuation member. Manual movement of the actuation member 148 may also be facilitated with use of an assisting device, such as a button, lever, switch, or other device that facilitates movement of the actuation member. Further, a clinician or operator may move the actuation member 148 automatically, such as with the use of a motor or other device operatively connected to the actuation member. Automatic movement of the actuation member 148 may be controlled, such as with a computer or other electronic device.

In one embodiment, a clinician or operator may manipulate movement of the snare relative to or through the second attachment member 182 by remotely moving the actuation member 148 of the snare in a direction towards the distal end of the endoscope 112 and/or away from the distal end of the endoscope. For example, when the actuation member 148 is moved toward the distal end of the endoscope 112 (e.g., in a direction $D_3$ as illustrated in FIG. 1), the snare is moved relative to or through the second attachment member 182 to at least partially close the loop 146. When the actuation member 148 is moved away from the distal end of the endoscope 112, the snare is moved relative to or through the second attachment member 182 to open the loop 146. In this regard, the elongated member(s) forming the loop 146 are moved toward the interior of the housing 102 and away from the longitudinal axis 130 of the housing or center of the cavity 108 to loosen or at least partially open the loop, thereby either reducing the blockage or obstruction of the cavity opening 110 or releasing its grip on a foreign body.

Remote manipulation of the snare may be, for example, by a manually operated cable or pulley, mechanical operation of a cable or pulley, or by other means of movement known in the art. For example, as illustrated in FIG. 1, the actuation member 148 is an elongated member, such as a cable or wire, that is operatively attached or integral with the loop 146 of the snare. The actuation member 148 extends through a channel of the endoscope 112, such as a working channel or auxiliary channel of the endoscope, from the distal end of the endoscope to a remote operating means. Operative attachment of the loop 146 to the actuation member 148 extending through the endoscope channel may be, for example, by a knot, clip, medical tape, snap fitting, compression fitting, or other suitable connecting means. It is also contemplated that the actuation member 148 may be operatively connected to and activated by a distally attached forceps tool, wherein manipulation of a forceps tool attached to the actuation member of the snare causes operable movement of the loop 146. For example, a forceps tool may be used to securely grasp at least a portion of the actuation member 148 of the snare.

As illustrated in FIG. 1, an optional third attachment point 144 may be used to movably attach the snare to the housing 102 of the retrieval device 100. As shown, the third attachment point 144 holds the snare adjacent to the interior of the housing 102 such that the snare is prohibited from interfering with a foreign body at least partially received in the cavity 108 of the retrieval device 100. In one embodiment, the third attachment point 144 comprises an attachment member, such as, for example, a loop, eyelet, or opening in the housing 102. The attachment member holds the actuation member 148 of the snare adjacent to the interior of the housing 102 and permits movement of the actuation member relative to or through the attachment member.

The snare may comprise a variety of medically suitable materials, such as, for example, ultra-high molecular weight polyethylene ("UHMWPE"), polycarbonate, stainless steel, titanium, titanium alloys, chromium-cobalt-molybdenum alloys, pyrocarbon, and combinations thereof. In various embodiments, the material of construction and the configuration of the snare, or portions thereof, are chosen to allow for unobstructed viewing of a foreign body.

Figure 3:
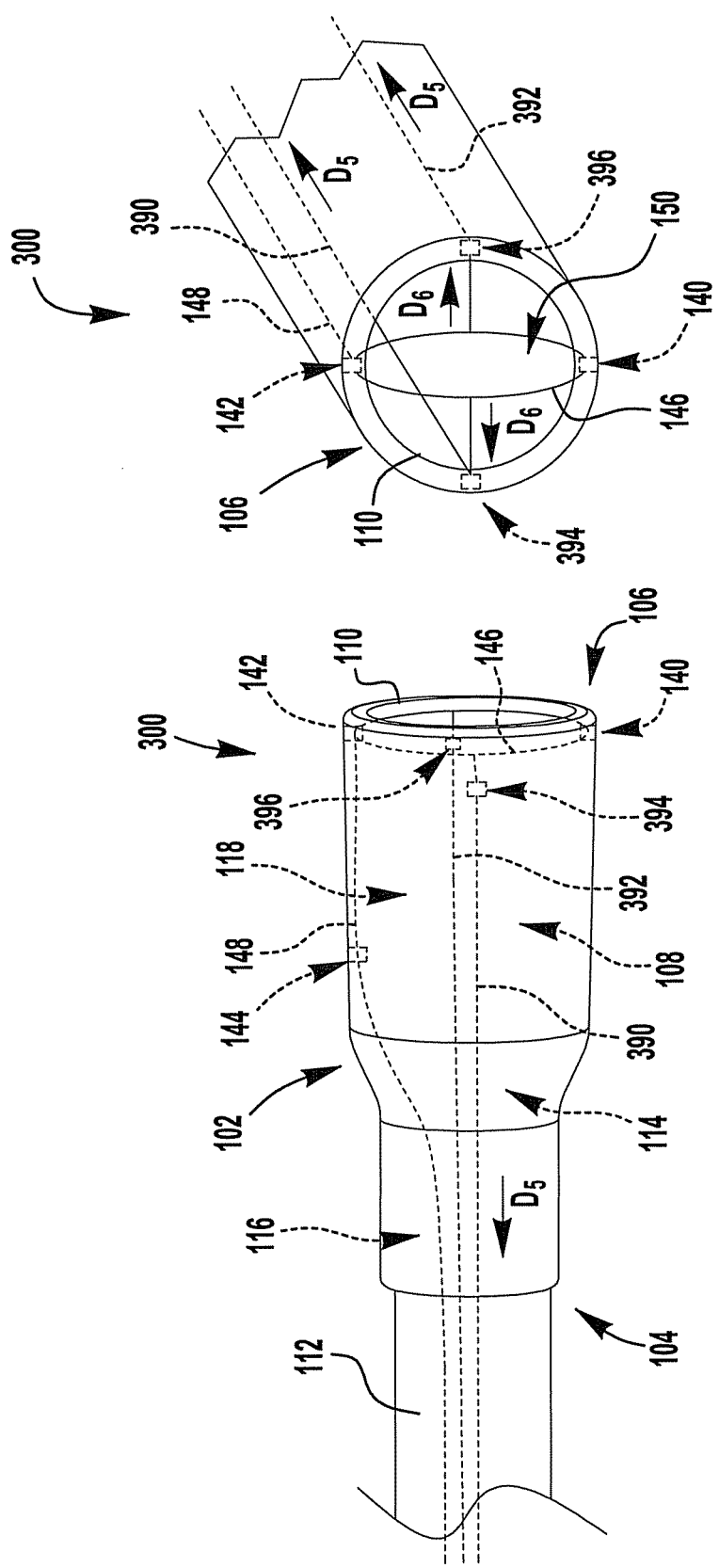
FIG. 3 illustrates a side view and a partial perspective view of a retrieval device according to an embodiment of the present application.

In certain embodiments, the retrieval device of the present application may comprise one or more actuation members for opening the loop of the snare after it has been partially closed. For example, FIG. 3 illustrates a retrieval device 300 having a snare that is movably attached to the housing 102 at a first attachment point 140 and a second attachment point 142. A loop 146 defining an at least partially closeable aperture 150 is formed between the first and second attachment points 140, 142. Moving a first actuation member 148 operatively attached or integral with the loop 146 moves the snare relative to the second attachment point 142 to at least partially close the loop.

As illustrated in FIG. 3, the retrieval device 300 comprises a second and third actuation member 390, 392 operatively attached or integral with the loop 146 of the snare. The second and third actuation members 390, 392 are also movably attached to third and fourth attachment points 394, 396, respectively. As shown, the third and fourth attachment points 394, 396 are diametrically opposed and located on the interior of the second portion 118 of the passage 114 adjacent the distal end 106 of the housing 102. The second and third actuation members 390, 392 extend through the passage 114 of the housing 102 and are movably connected to the distal end of the endoscope 112. For example, the actuation members 390, 392 may extend through a channel of the endoscope 112, such as a working channel or auxiliary channel of the endoscope, from the distal end of the endoscope to a remote operating means.

The third and fourth attachment points 394, 396 generally comprise one or more attachment members, e.g., an eyelet, loop, hook, one or more openings, clip, or other device or fastener, extending from or disposed within the housing 102 of the retrieval device 100. As illustrated in FIG. 3, moving the second and third actuation members 390, 392 in a direction $D_5$ and relative to or through the third and fourth attachment points 394, 396, respectively, opens the loop 146. In this regard, the elongated member(s) forming the loop 146 are moved in a direction $D_6$ toward the interior of the housing 102 and away from the longitudinal axis of the housing or center of the cavity 108 to loosen or at least partially open the loop 146, thereby either reducing the blockage or obstruction of the cavity opening 110 or releasing its grip on a foreign body.

FIGS. 4A-7B illustrate a retrieval device 400 according to an embodiment of the present application. The retrieval device 400 comprises a snare disposed within the cavity 408 of the housing 402 and movable relative to the housing. The snare comprises a loop 546 that defines an at least partially closeable aperture 550. The at least partially closeable aperture 550 is completely defined by the snare. The snare also comprises an actuation member 548 operatively attached or integral with the loop 546 of the snare. The actuation member 548 extends through the passage 414 of the housing 402 and one or more channels of the endoscope 510 to a remote operating means. As shown in FIGS. 5A-7B, the snare also comprises a sheath 570. At least a portion of the actuation member 548 is housed or disposed within the sheath 570 and is movable relative to the sheath.

Figure 4A:
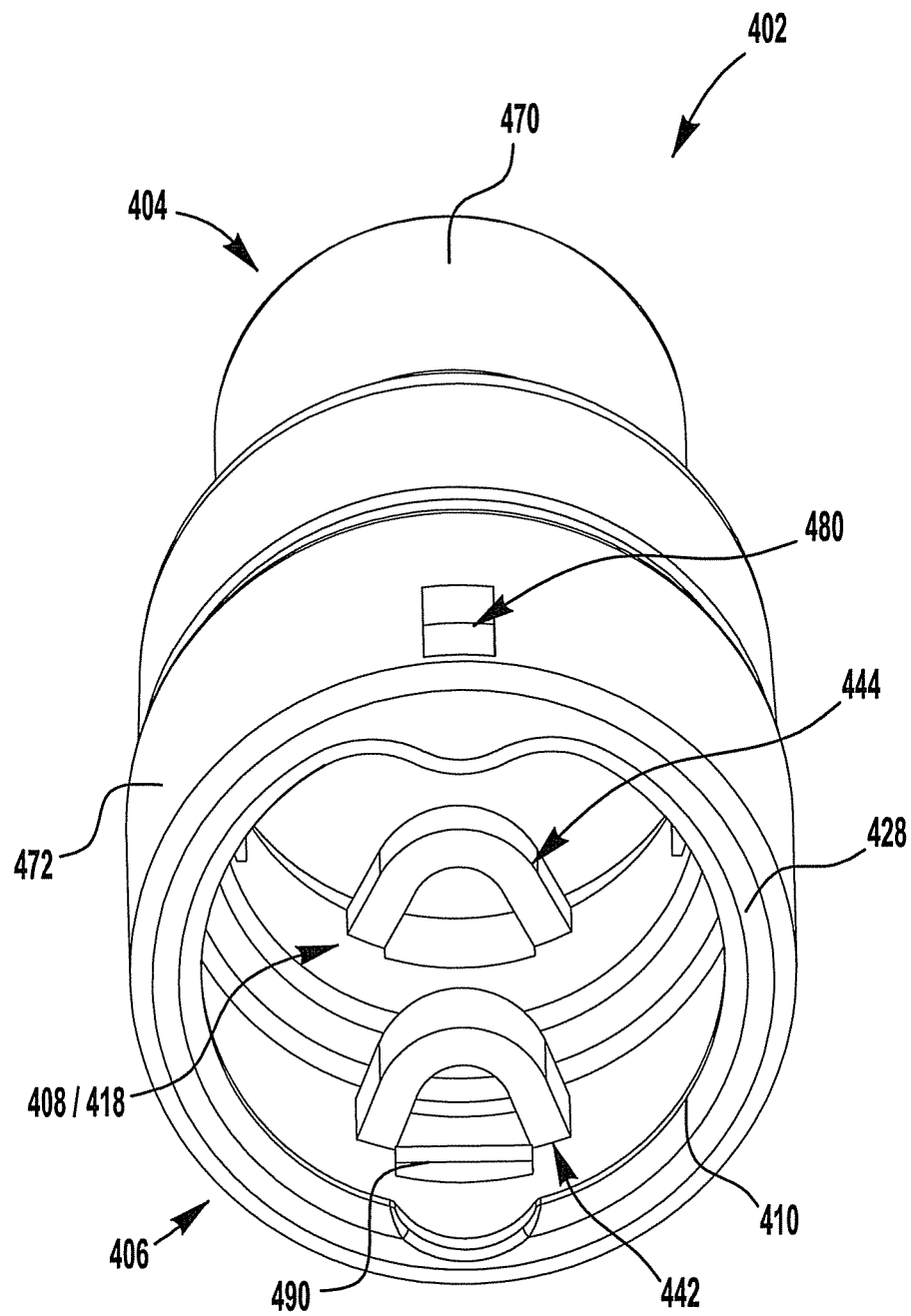
FIGS. 4A-4C are top perspective, bottom perspective, and end views of a retrieval device housing according to an embodiment of the present application.
Figure 4B:
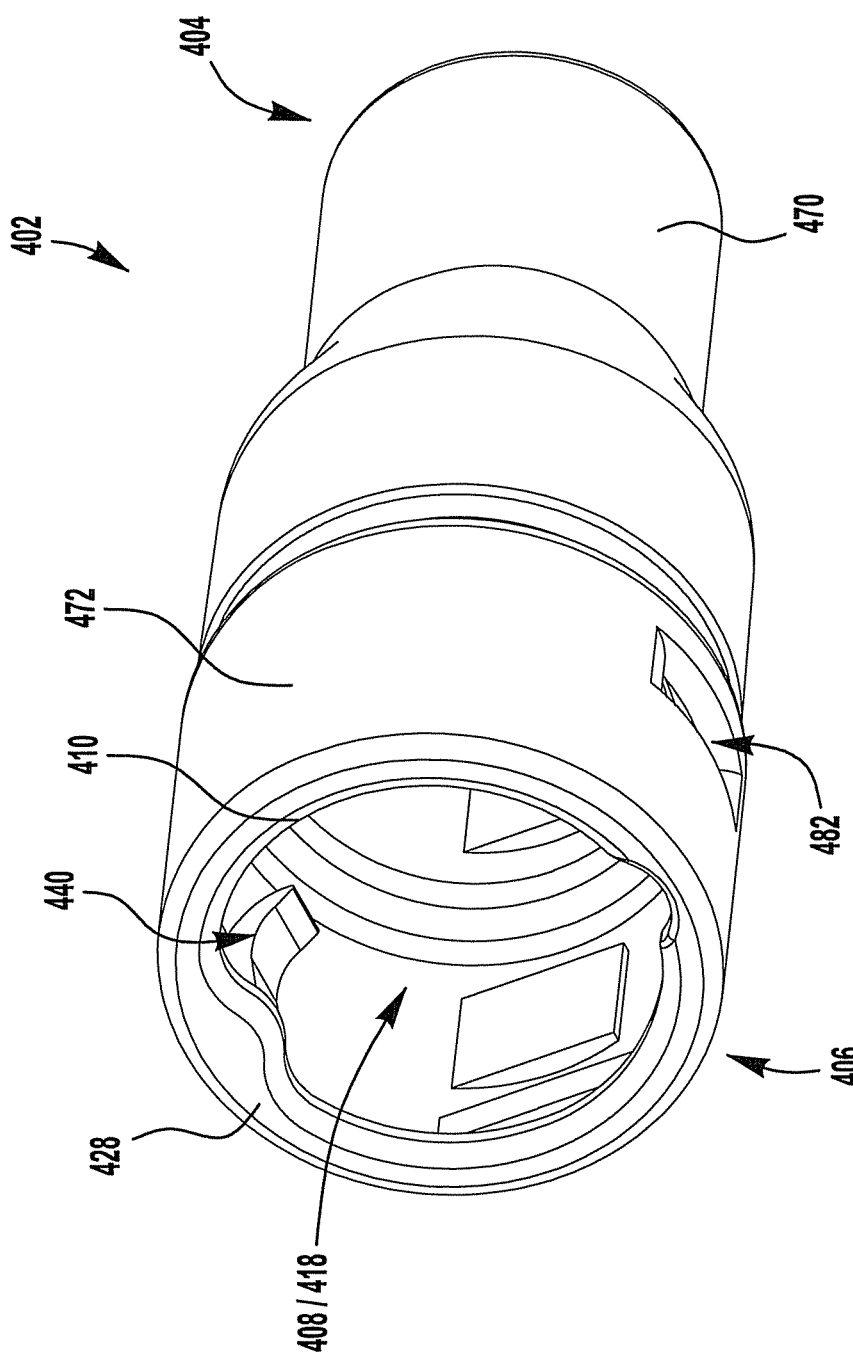
Figure 4C:
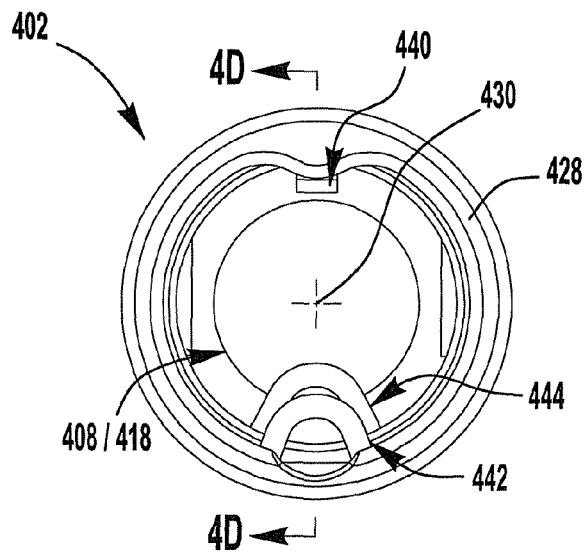
Figure 4D:
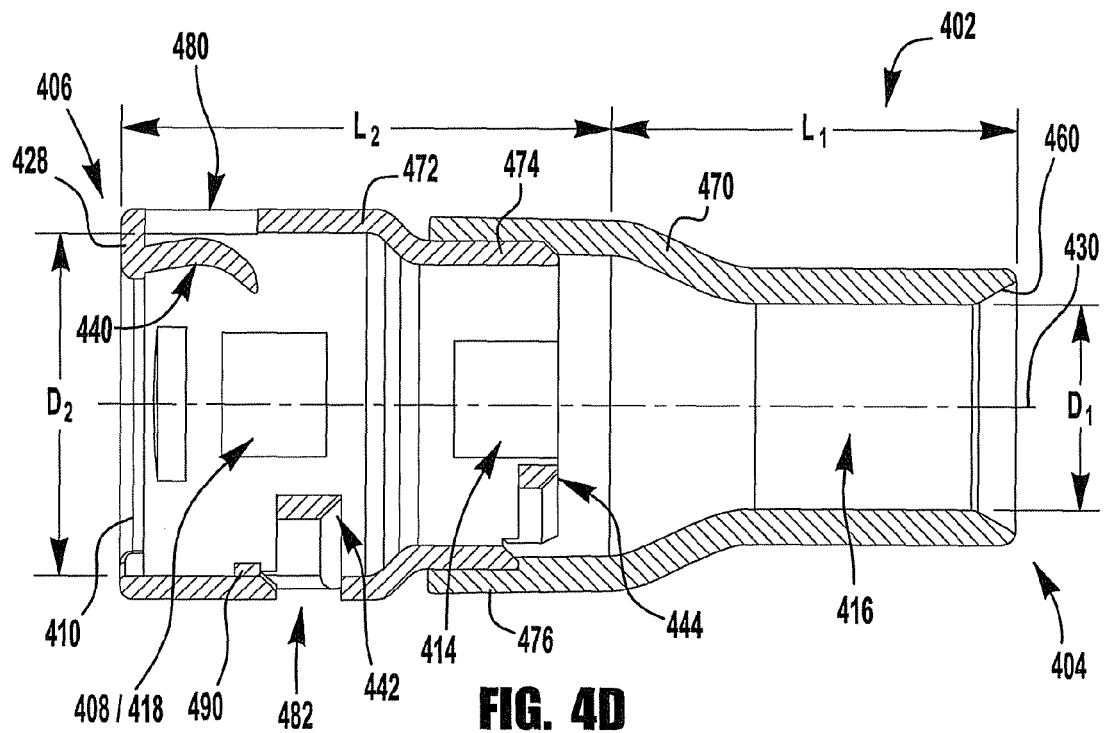
FIG. 4D is a side cross sectional view of the retrieval device housing of FIGS. 4A-4C, wherein the cross section is taken along line 4D-4D shown in FIG. 4C.
Figure 5A:
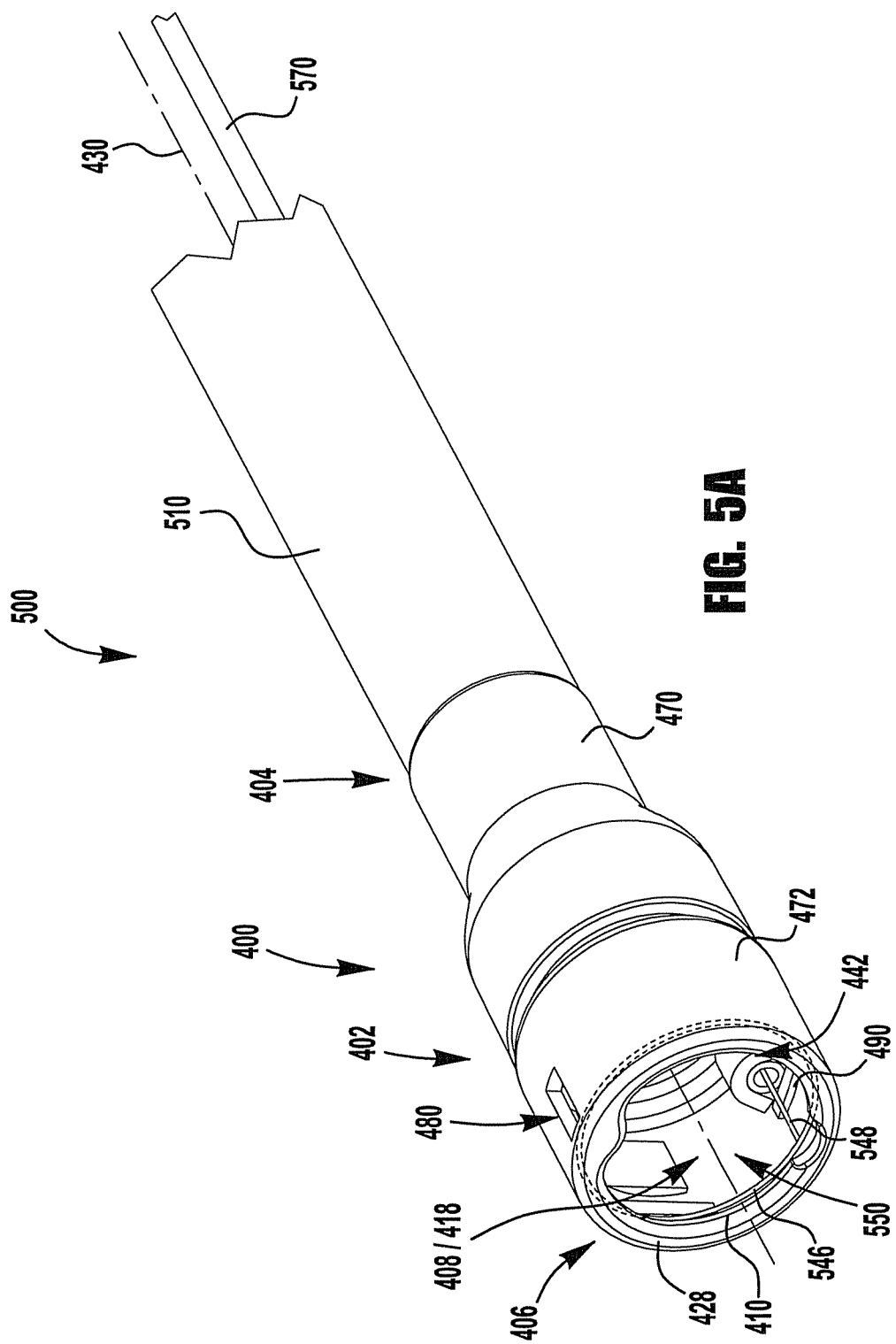
FIG. 5A is a partial perspective view of a retrieval system according to an embodiment of the present application.
Figure 5B:
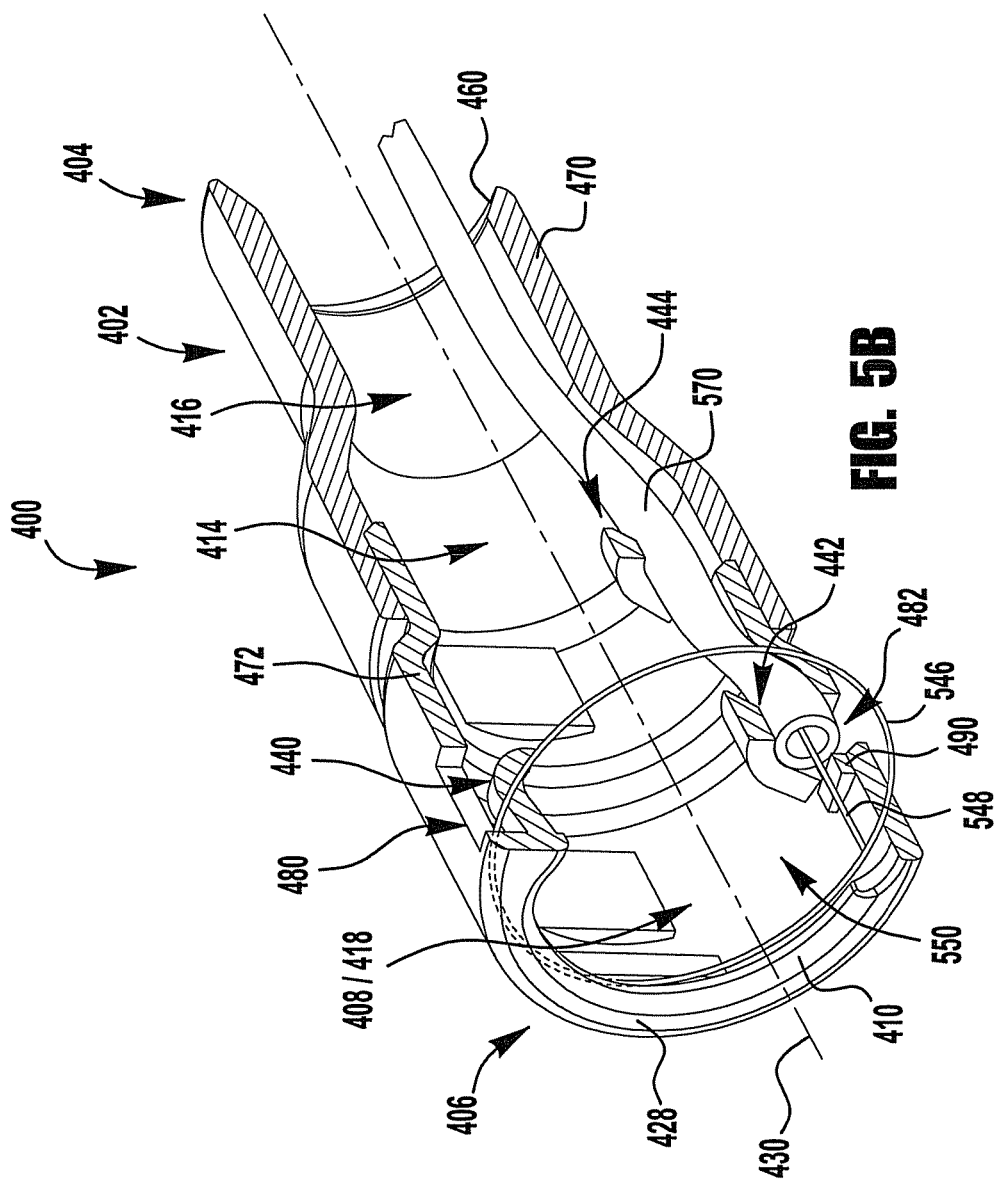
FIG. 5B is a partial perspective cross sectional view of a retrieval device of the retrieval system of FIG. 5A according to an embodiment of the present application.

As illustrated in FIGS. 4A-4D, the housing 402 of the retrieval device 400 comprises a first attachment member 440, a second attachment member 442, and an optional third attachment member 444. In certain embodiments, the first attachment member 440 is formed as a hook or clip and extends from the interior of the housing 402 although other configurations are possible. As shown in FIG. 4D, the first attachment member 440 extends longitudinally from the interior of the flanged portion 428 of the housing 402 and curves downward toward the longitudinal axis 430 of the housing or the center of the cavity 408. The second and third attachment members 442, 444 are diametrically opposed to the first attachment member 440. As shown in FIGS. 4A and 4C, the second and third attachment members 442, 444 are formed as loops or arches that extend from the interior of the housing 402 and toward the longitudinal axis 430 of the housing or the center of the cavity 408.

The first, second, and third attachment members 440, 442, 444 movably attach the snare to the housing 402 of the retrieval device 400. As illustrated in FIGS. 5A and 7A-7B, the loop 546 of the snare is movably attached to the first attachment member 440. As shown, the loop 546 is hung on the hook or clip extending from the interior of the housing 402 to attach the snare to the housing. The housing 402 may comprise one or more optional openings 480 adjacent to the first attachment member 440 that may be used to facilitate attachment of the loop 546 on the hook or clip.

Further, as illustrated in FIGS. 5A and 7A-7B, the snare is movably attached to the second and third attachment members 442, 444. As shown, the snare is disposed within openings formed by the second and third attachment members 442, 444 of the housing 402. The second and third attachment members 442, 444 are configured to prohibit radial movement of the sheath 570 relative to the housing 402 of the retrieval device 400. Further, an optional stop 490 located adjacent to the opening formed by the second attachment member 442 is configured to prohibit longitudinal movement of the sheath 570 relative to the housing 402. The housing 402 may comprise one or more optional openings 482 adjacent to the second or third attachment members 442, 444 that may be used to facilitate attachment of the snare to the housing of the retrieval device 400.

Moving the actuation member 548 of the snare relative to or through the second attachment member 442 or sheath 570 at least partially closes the loop 546 of the snare. For example, a clinician or operator may remotely move the actuation member 548 in a direction towards the distal end of the endoscope 510 and/or away from the distal end of the endoscope. Moving the actuation member 548 toward the distal end of the endoscope 510 at least partially closes the loop 546 and moving the actuation member away from the distal end of the endoscope opens the loop.

Figure 6A:
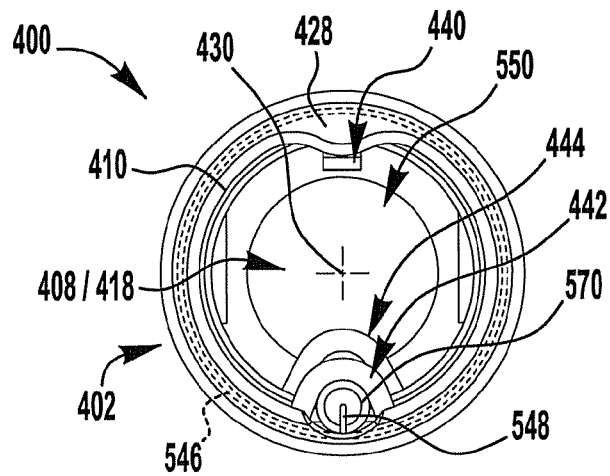
FIGS. 6A-6C are end views of the retrieval device of FIG. 5B showing movement of a capture tool according to an embodiment of the present application.
Figure 6B:
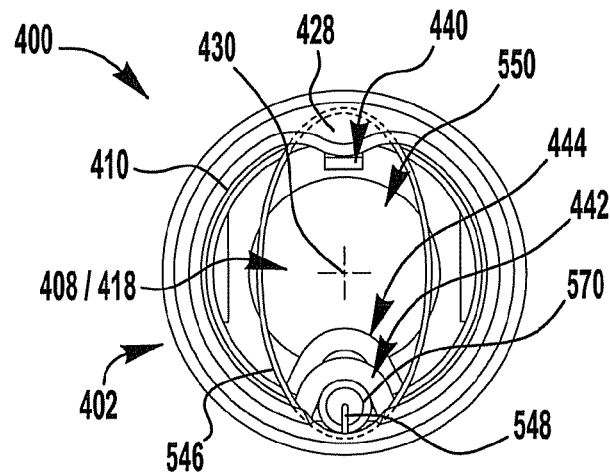
Figure 6C:
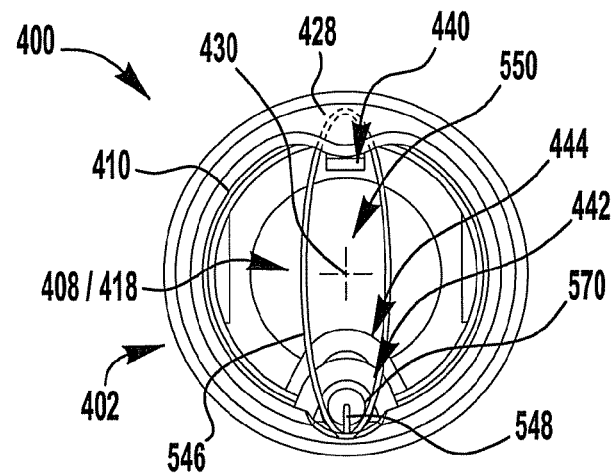

FIGS. 6A-6C are end views of the retrieval device 400 illustrating the movement of the loop 546 as the actuation member 548 is moved relative to or through the second attachment member 442 or sheath 570. FIG. 6A illustrates the snare in a first position, such as, for example, when the snare is at rest or not actuated by a clinician. As shown, the loop 546 of the snare is disposed within the housing 402 in the space behind the flanged portion 428 of the housing. As such, the loop 546 does not block or obstruct the cavity opening 410 at the distal end 406 of the housing 402. In the first position, the at least partially closeable aperture 550 defined by the loop 546 is larger than the cavity opening 410 such that the opening is not obstructed.

FIGS. 6B and 6C illustrate the snare in a second position, wherein the loop 546 of the snare is at least partially closed. As the actuation member 548 is moved relative to or through the second attachment member 442 or sheath 570, the elongated member(s) forming the loop 546 are moved toward the longitudinal axis 430 of the housing 402 or center of the cavity 408 to tighten or at least partially close the loop. Further, the aperture 550 defined by the loop 546 is at least partially closed as the actuation member 548 is moved relative to or through the second attachment member 442 or sheath 570. In the second position, the loop 546 of the snare at least partially blocks or obstructs the opening 410 in the distal end 406 of the housing 402. Further, the loop 546 of the snare may hold or grasp at least a portion of a foreign body that is at least partially received in the loop or the at least partially closeable aperture 550 defined by the loop.

FIGS. 7A and 7B illustrate the retrieval device 400 with a foreign body 700 captured, blocked, or otherwise secured within at least a portion of the housing 402. As illustrated in FIG. 7A, a portion of the foreign body 700 is received within the cavity 408 of the housing 402. Further, at least a portion of the foreign body 700 is captured within the loop 546 that defines the at least partially closeable aperture 550. As illustrated in FIG. 7B, the foreign body 700 is received within the cavity 408 of the housing 402 and the loop 546 at least partially blocks or obstructs the opening 410 in the distal end 406 of the housing 402.

The snare may be comprised of any medically suitable material. For example, ultra-high molecular weight polyethylene ("UHMWPE"), polycarbonate, stainless steel, titanium, titanium alloys, chromium-cobalt-molybdenum alloys, pyrocarbon, and combinations thereof. In various embodiments, the material of construction and the configuration of the snare, or portions thereof, are chosen to allow for unobstructed viewing of a foreign body.

Further, the retrieval device 400 may be configured for use with a variety of conventional endoscopic snares, such as, for example, snares having oval, circular, crescent, and/or hexagonal shaped loop portions of various opening and sheath diameters manufactured by various medical device companies. For example, a conventional snare may be routed through a channel of the endoscope 510, such as a working channel or auxiliary channel of the endoscope, and through the second and third attachment members 442, 444 of the housing 402. The loop portion of the conventional snare may then be attached to the first attachment member 440 such that movement of the snare relative to the second attachment member 442 or sheath of the snare at least partially closes the loop portion.

The retrieval devices of the present application may comprise a capture tool having one or more grasping members, such as, for example a rake or other toothed structure, that may be remotely manipulated by a clinician or operator to capture, block, or otherwise secure a foreign body within at least a portion of the housing. In certain embodiments, the grasping member and the housing define an at least partially closeable aperture. In other embodiments, first and second grasping members of the capture tool define an at least partially closeable aperture.

Figure 8A:
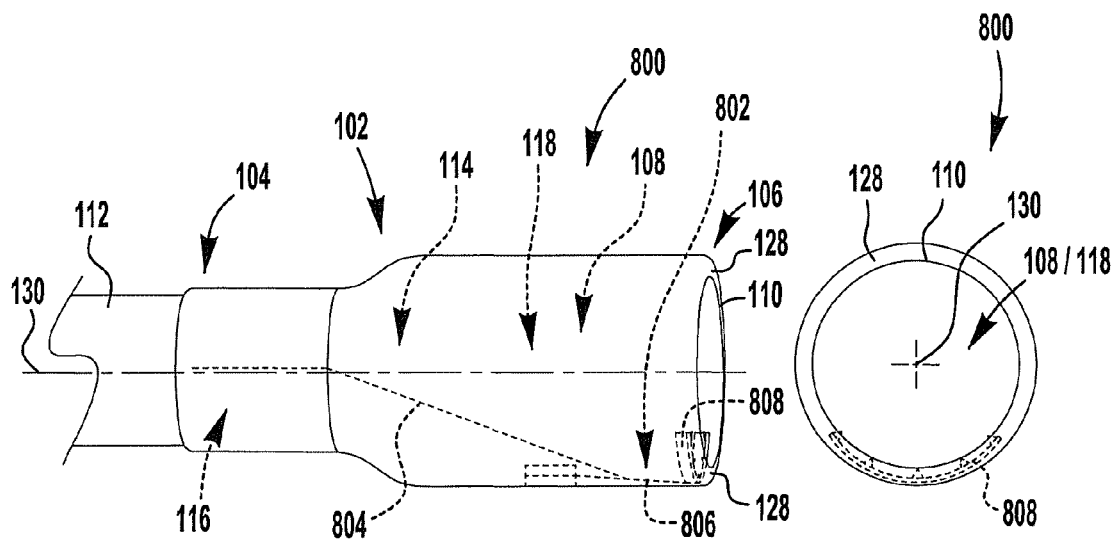
FIGS. 8A and 8B illustrate side and end views of a retrieval device according to an embodiment of the present application.
Figure 8B:
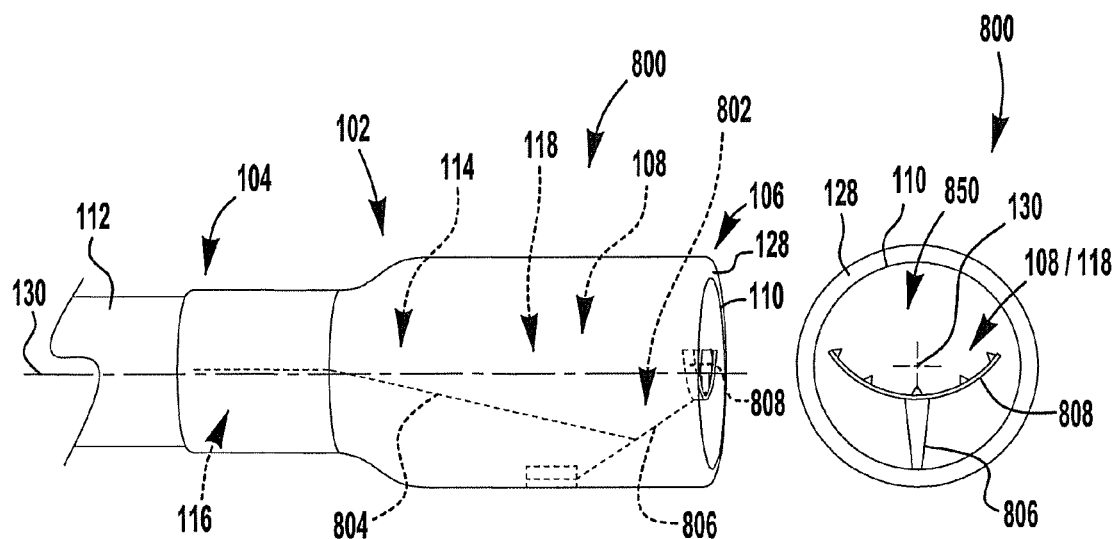

For example, FIGS. 8A and 8B illustrate a retrieval device 800 having a grasping member 802 disposed within the cavity 108 of the housing 102 and movable relative to the housing. As shown, the grasping member 802 is pivotally attached to the housing 102 for movement between a first position shown in FIG. 8A and a second position shown in FIG. 8B. An actuation member 804 is operatively attached or integral with the grasping member 802. The actuation member 804 extends through the passage 114 of the housing 102 and is movably connected to the distal end of the endoscope 112.

As illustrated in FIGS. 8A and 8B, a first portion 806 of the grasping member 802 is pivotally attached to the interior of the housing 102 and a second portion 808 is adapted to grip a foreign body. As shown, the second portion 808 of the grasping member 802 comprises one or more teeth. However, other gripping means (e.g., spikes or splines) or no gripping means are also contemplated. Further, the second portion 808 of the grasping member 802 may be movably attached to the first portion 806. For example, as illustrated in FIGS. 8A and 8B, the second portion 808 may be configured to pivot relative to the first portion 806 as the grasping member 802 is moved from the first position to the second position. The second portion 808 may be movably attached to the first portion 806 of the grasping member 802 in a variety of ways. For example, attachment may be by a spring, hinge, pin, or other means allowing for movement of the second portion 808 in response to movement of the first portion 806.

It is contemplated that a clinician or operator may manipulate movement of the grasping member 802 by remotely moving the actuation member 804. For example, a clinician or operator may move the actuation member 804 manually, such as by pulling, twisting, or pushing the actuation member or one or more members operatively connected to the actuation member. Manual movement of the actuation member 804 may also be facilitated with use of an assisting device, such as a button, lever, switch, or other device that facilitates movement of the actuation member. Further, a clinician or operator may move the actuation member 804 automatically, such as with the use of a motor or other device operatively connected to the actuation member. Automatic movement of the actuation member 804 may be controlled, such as with a computer or other electronic device.

In one embodiment, a clinician or operator may manipulate movement of the grasping member 802 by remotely moving the actuation member 804 in a direction toward the distal end of the endoscope 112 or away from the distal end of the endoscope. For example, remote manipulation may be by manually-operated cable or pulley, mechanical operation of a cable or pulley, or by other means of movement known in the art. In certain embodiments, when the actuation member 804 is moved toward the distal end of the endoscope 112, the second portion 808 of the grasping member 802 moves from the first position shown in FIG. 8A to the second position shown in FIG. 8B. In this regard, the second portion 808 of the grasping member 802 moves away from the interior of the housing 102 and towards the longitudinal axis 130 or center of the cavity 108, thereby either blocking at least a portion of the cavity or gripping at least a portion of a foreign body. As such, an at least partially closeable aperture 850 is formed between the second portion 808 of the grasping member 802 and the housing 102. When the actuation member 804 is moved away from the distal end of the endoscope 112, the second portion 808 of the grasping member 802 moves back toward the interior of the housing 102 and away from the center of the cavity 108, thereby either reducing the blockage or obstruction of the cavity or releasing its grip on a foreign body.

Figure 9A:
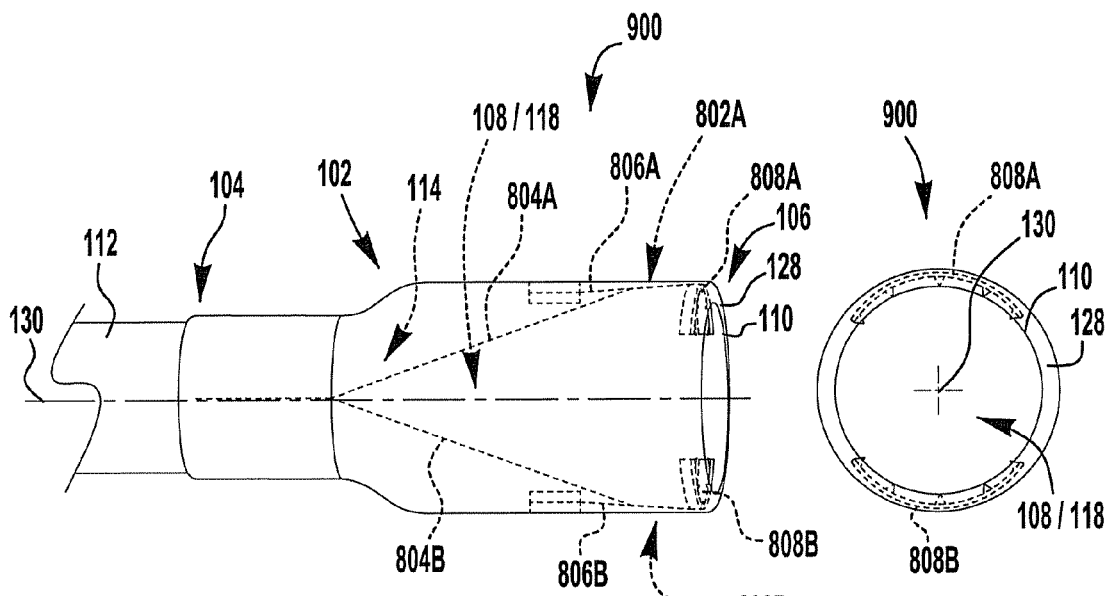
FIGS. 9A and 9B illustrate side and end views of a retrieval device according to an embodiment of the present application.
Figure 9B:
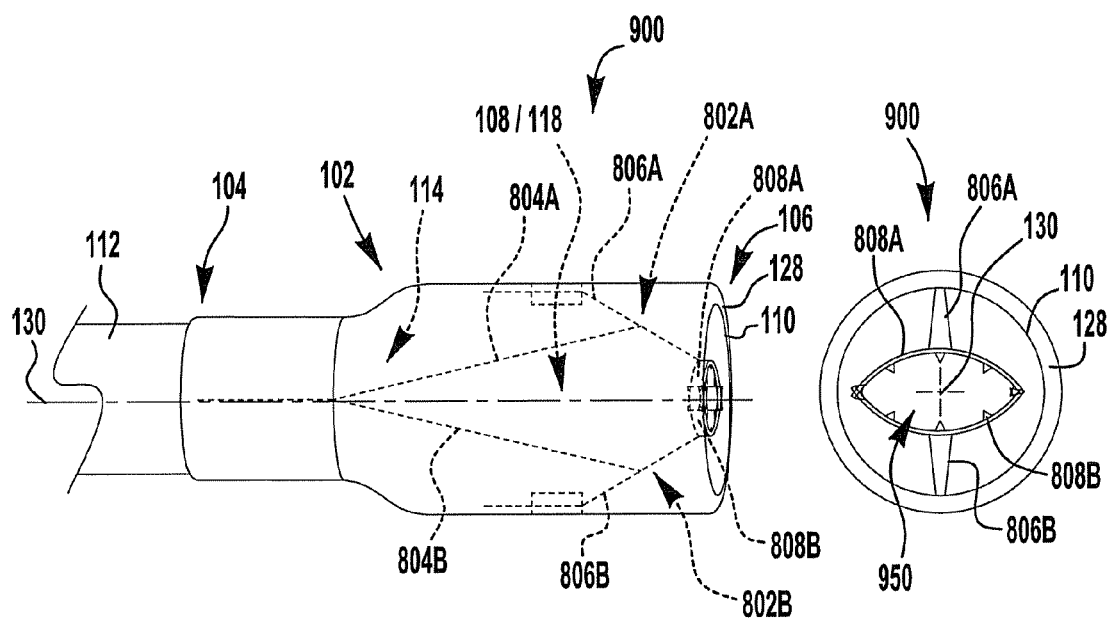

FIGS. 9A and 9B illustrate a retrieval device 900 having a plurality of grasping members 802A, 802B disposed within the cavity 108 of the housing 102 and movable relative to the housing. As shown, first and second grasping members 802A, 802B are pivotally attached to the housing 102 for movement between a first position shown in FIG. 9A and a second position shown in FIG. 9B. First and second actuation members 804A, 804B are operatively attached or integral with the grasping members 802A, 802B, respectively. The actuation members 804A, 804B extend through the passage 114 of the housing 102 and are movably connected to the distal end of the endoscope 112.

As illustrated in FIGS. 9A and 9B, a first portion 806A, 806B of each grasping member 802A, 802B is pivotally attached to the interior of the housing 102 and a second portion 808A, 808B of each grasping member is adapted to grip a foreign body. In certain embodiments, when the actuation members 804A, 804B are moved towards the distal end of the endoscope 112, the second portions 808A, 808B of the grasping members 802A, 802B move from the first position shown in FIG. 9A to the second position shown in FIG. 9B. In this regard, the second portions 808A, 808B of the grasping members 802A, 802B move away from the interior of the housing 102 and towards the longitudinal axis 130 or center of the cavity 108, thereby either blocking at least a portion of the cavity or gripping at least a portion of a foreign body. As such, the first and second grasping members 802A, 802B define an at least partially closeable aperture 950. When the actuation members 804A, 804B are moved away from the distal end of the endoscope 112, the second portions 808A, 808B of the grasping members 802A, 802B move back toward the interior of the housing 102 and away from the center of the cavity 108, thereby either reducing the blockage or obstruction of the cavity or releasing their grip on a foreign body.

Remote manipulation of any one or more grasping member may be, for example, by a manually operated cable or pulley, mechanical operation of a cable or pulley, or by other means of movement known in the art. For example, as illustrated in FIGS. 8A-9B, the actuation members are elongated members, such as a cable or wire, that are operatively attached or integral with the grasping members. The actuation members extend through a channel of the endoscope, such as a working channel or auxiliary channel of the endoscope, from the distal end of the endoscope to a remote operating means. Operative attachment of the grasping member to the actuation member may be, for example, by a knot, clip, medical tape, snap fitting, compression fitting, or other suitable connecting means. It is also contemplated that the actuation member may be operatively connected to and activated by a distally attached forceps tool, wherein manipulation of a forceps tool attached to the actuation member causes operable movement of the grasping member. For example, a forceps tool may be used to securely grasp at least a portion of the actuation member.

The actuation members and the grasping members, portions thereof, or combinations thereof may be comprised of any medically suitable material. For example, ultra-high molecular weight polyethylene ("UHMWPE"), polycarbonate, stainless steel, titanium, titanium alloys, chromium-cobalt-molybdenum alloys, pyrocarbon, and combinations thereof. In various embodiments, the material of construction and the configuration of the capture tool, or portions thereof, are chosen to allow for unobstructed viewing of a foreign body.

The foreign body retrieval systems of the present application may comprise an endoscope having a distal end for insertion into a patient and a retrieval device of the present application attached to the distal end of the endoscope. For example, FIG. 5A illustrates an exemplary foreign body retrieval system 500 according to an embodiment of the present application. As shown, the retrieval device 400 is attached to the distal end of the endoscope 510. The retrieval device 400 comprises a housing 402 and a capture tool. The housing 402 has at least one cavity 408 and an opening 410 for at least partially receiving a foreign body. The capture tool is disposed within and movable relative to the housing 402 and defines an at least partially closeable aperture 550. In certain embodiments, at least a portion of the capture tool is operatively connected to a remote operating device for moving the capture tool relative to the housing. For example, at least a portion of the capture tool may be operatively connected to a cable disposed in a channel of the endoscope to facilitate remote operation of the capture tool. Movement of the cable relative to the channel moves the capture tool relative to the housing. In certain embodiments, the channel of the endoscope 510 has a diameter between about 1.9 mm and 4.0 mm. For example, the channel of the endoscope may be about 2.8 mm, greater than or equal to about 3.2 mm if a therapeutic channel is used, or between about 2.0 and 2.2 mm for pediatric endoscopes. Further, the endoscope may be configured to selectively apply a suction through one or more channels of the endoscope. The suction facilitates movement of at least a portion of the foreign body into the opening and the at least one cavity of the housing. The endoscope may also comprise a visualization means, such as a camera or lens, for visualization of the foreign body. At least a portion of the housing may comprise a transparent material to facilitate visualization of the foreign body.

One example of an endoscopic foreign body retrieval procedure involves sedating a patient and inserting an endoscope through the mouth of the patient and advancing it through the esophagus and/or stomach until identification of the foreign body is obtained. At least a portion of the foreign body is grasped or otherwise secured using a retrieval device of the present application. The endoscope and the secured foreign body is removed from the patient. Optionally, tissue injury may be evaluated or another follow-up procedure may be performed.

The patient is then awakened from sedation.

One exemplary method of retrieving a foreign body from the esophagus of a patient includes inserting a distal end of an endoscope into a patient's mouth, wherein a retrieval device of the present application is attached to the distal end of the endoscope. The retrieval device comprises a housing and a capture tool. The housing has at least one cavity and an opening for at least partially receiving a foreign body. The capture tool is disposed within and movable relative to the housing and defines an at least partially closeable aperture. The distal end of the endoscope and the retrieval device are advanced through the esophagus of the patient. At least a portion of a foreign body is received in the at least one cavity of the housing. The capture tool is moved relative to the housing to at least partially close the aperture defined by the capture tool. The distal end of the endoscope and the retrieval device are removed from the patient to retrieve the foreign body. In certain embodiments, moving the capture tool relative to the housing at least partially blocks the opening in the housing to prohibit removal of the foreign body from the at least one cavity. Further, moving the capture tool relative to the housing may hold at least a portion of the foreign body within the at least one cavity. The method may include using a visualization device, such as a camera or lens, of the endoscope to visualize the foreign body. Further, a suction device of the endoscope may be used to facilitate receipt of the foreign body in the at least one cavity. The opening in the housing may also be moved towards the foreign body to facilitate receipt of the foreign body in the at least one cavity.

Another exemplary method of removing an esophageal foreign body from a patient includes using an esophageal foreign body retrieval device removably attached to a distal end of an endoscope. The retrieval device comprises a housing and a movable capture tool, as illustrated in any one of FIGS. 1-7B. The capture tool is mechanically connected to a wire or cable running from the proximal end of the endoscope to the distal end through the working channel, wherein movement of the capture tool is actuated by a clinician via an operating means mechanically attached to the proximal end of the cable.

The exemplary method includes inserting an endoscope comprising the retrieval device through the patient's mouth and advancing it through the esophagus until the foreign body can be visualized using the endoscope visualization means (e.g. camera). Suction and movement of the retrieval device toward the foreign body is employed to promote entrance of at least a portion of the foreign body into the cavity opening of the retrieval device housing. Once the foreign body is properly positioned within the cavity opening (or portion thereof), the clinician actuates movement of the cable to at least partially close the loop of the snare, thereby either blocking at least a portion of the cavity or securely gripping at least a portion of the foreign body. Preferably, the foreign body is fully secured within the cavity of the retrieval device. Once control over the foreign body is established using the snare capture tool and suction, the scope is removed from the patient while maintaining control over the foreign body. Visualization of the foreign body using the endoscope's visualization means may be maintained while the endoscope is removed from the patient. Once the foreign body is removed, the steps may be repeated to confirm that all portions of the foreign body have been removed, to inspect for tissue trauma, to biopsy the mucosa, or combinations thereof.

Another exemplary method of removing an esophageal foreign body from a patient includes using an esophageal foreign body retrieval device removably attached to a distal end of an endoscope. The retrieval device comprises a housing and a movable capture tool, as illustrated in any one of FIGS. 8A-9B. The capture tool is mechanically connected to a wire or cable running from the proximal end of the endoscope to the distal end through the working channel, wherein movement of the capture tool is actuated by a clinician via an operating means mechanically attached to the proximal end of the cable.

The exemplary method includes inserting an endoscope comprising the retrieval device through the patient's mouth and advancing it through the esophagus until the foreign body can be visualized using the endoscope visualization means (e.g. camera). Suction and movement of the retrieval device toward the foreign body is employed to promote entrance of at least a portion of the foreign body into the cavity opening of the retrieval device housing. Once the foreign body is properly positioned within the cavity opening (or portion thereof), the clinician actuates movement of the cable to move the grasping member toward to the center of the cavity, thereby either blocking at least a portion of the cavity or securely gripping at least a portion of the foreign body. Preferably, the foreign body is fully secured within the cavity of the retrieval device. Once control over the foreign body is established using the grasping member capture tool and suction, the scope is removed from the patient while maintaining control over the foreign body. Visualization of the foreign body using the endoscope's visualization means may be maintained while the endoscope is removed from the patient. Once the foreign body is removed, the steps may be repeated to confirm that all portions of the foreign body have been removed, to inspect for tissue trauma, to biopsy the mucosa, or combinations thereof.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities, properties, conditions, and so forth as used in the specification and claims are to be understood as being modified in all instances by the term "about." Additionally, the disclosure of any ranges in the specification and claims are to be understood as including the range itself and also anything subsumed therein, as well as endpoints. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

As described herein, when one or more components are described as being connected, joined, affixed, coupled, attached, or otherwise interconnected, such interconnection may be direct as between the components or may be in direct such as through the use of one or more intermediary components. Also as described herein, reference to a "member," "component," or "portion" shall not be limited to a single structural member, component, or element but can include an assembly of components, members or elements.

While the present invention has been illustrated by the description of embodiments thereof, and while the embodiments have been described in considerable detail, it is not the intention of the applicants to restrict or in any way limit the scope of the invention to such details. Additional advantages and modifications will readily appear to those skilled in the art. For example, where components are releasably or removably connected or attached together, any type of releasable connection may be suitable including for example, locking connections, fastened connections, tongue and groove connections, etc. Still further, component geometries, shapes, and dimensions can be modified without changing the overall role or function of the components. Therefore, the inventive concept, in its broader aspects, is not limited to the specific details, the representative apparatus, and illustrative examples shown and described. Accordingly, departures may be made from such details without departing from the spirit or scope of the applicant's general inventive concept.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, devices and components, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure, however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention, the inventions instead being set forth in the appended claims. Descriptions of exemplary methods or processes are not limited to inclusion of all steps as being required in all cases, nor is the order that the steps are presented to be construed as required or necessary unless expressly so stated.

We claim:

1. A foreign body retrieval device capable for use in retrieving a foreign body with an endoscope, comprising:
a housing comprising a wall made of a rigid, semi-rigid or semi-flexible material having a proximal end, a distal end, and at least one cavity, wherein the proximal end of the housing is configured for attachment to a distal end of an endoscope and the distal end comprises a cavity opening for at least partially receiving a foreign body in the at least one cavity; and
a capture tool comprising an actuation member coupled to the housing and a loop extending from the actuation member, wherein the loop defines an at least partially closeable aperture, wherein one side of the loop extends from the actuation member and an opposite side of the loop, opposite of the one side of the loop, is attached to a portion of the housing opposite of where the actuation member is coupled to the housing and at a distance from where the actuation member is coupled to the housing, such that the loop comprises a plurality of elongated members, each of the plurality of elongated members forming a portion of the at least partially closeable aperture for the opening at the distal end of the housing, each of the plurality of elongated members extending between the one side of the loop and the opposite side of the loop where the opposite side of the loop is attached to the portion of the housing, wherein the plurality of elongated members are extendable, such that the opening is not obstructed by the loop in a first position of the capture tool, and closeable such that the at least partially closeable aperture is at least partially closed by the plurality of elongated members of the loop in a second position of the capture tool, engaging the foreign body, while the opposite side of the loop remains attached to the housing during use, without changing the distance between the one side of the loop and the opposite side of the loop.

2. The retrieval device according to claim 1, wherein the plurality of elongated members are configured to hold at least a portion of the foreign body within the at least one cavity.

3. The retrieval device according to claim 1, wherein the housing defines a passage extending from the proximal end of the housing to the distal end of the housing along a longitudinal axis of the housing, and wherein a first portion of the passage is configured for attachment to the distal end of the endoscope and a second portion of the passage defines the at least one cavity.

4. The retrieval device according to claim 1, further comprising a channel coupled to the cavity of the housing, wherein the channel provides suction from a suction device through the channel.

5. The retrieval device according to claim 1, wherein the opposite side of the loop is coupled to the housing at a first attachment member extending from an interior of the housing.

6. The retrieval device of claim 5, wherein the first attachment member comprises a hook and the housing comprises a radial opening adjacent to the hook to facilitate attachment of the loop on the hook.

7. The retrieval device according to claim 5, wherein the actuation member is at least partially housed in a sheath and is movable relative to the sheath and wherein the sheath is attached at a second attachment point extending from the housing, and the second attachment point is configured to prohibit radial movement of the sheath relative to the housing, and wherein moving the actuation member relative to the sheath at least partially extends or retracts the loop, wherein the plurality of elongated members between the first attachment point and the second attachment point are extendable or closeable, respectively, when the loop is at least partially extended from the sheath or retracted into the sheath, while the opposite side of the loop remains attached to the housing.

8. The retrieval device according to claim 7, wherein the second attachment point comprises a second attachment member extending from the interior of the housing and configured to prohibit radial movement of the sheath relative to the housing.

9. The retrieval device according to claim 8, wherein the sheath is disposed within an opening formed by the second attachment member, and wherein the housing further comprises a stop configured to prohibit longitudinal movement of the sheath relative to the housing.

10. The retrieval device according to claim 1, further comprising a grasping device, wherein at least a portion of the grasping device is pivotally attached to the housing.

11. The retrieval device according to claim 10, wherein the grasping device comprises a first portion and a second portion, opposite of the first portion, wherein both the first portion and the second portion of the grasping device are pivotally attached to the housing and pivotally close together when actuating member is actuated.

12. The device of claim 1, wherein the housing is comprised of a silicone material.

13. A foreign body retrieval system, comprising:
an endoscope having a distal end for insertion into a patient; and
a retrieval device comprising a housing and a capture tool, the housing having at least one cavity and a cavity opening for at least partially receiving a foreign body, the capture tool at least partially disposed within and movable relative to the housing and defining an at least partially closeable aperture, wherein the housing has a proximal end attached to the distal end of the endoscope and a distal end defining the opening for at least partially receiving a foreign body in the at least one cavity, and the capture tool comprises an actuation member coupled to the housing and a loop extending from the actuation member, wherein one side of the loop is attached to the actuation member and an opposite side of the loop, opposite of the one side of the loop, is attached to a portion of the housing opposite of where the actuation member is coupled to the housing and at a distance from where the actuation member is coupled to the housing, defining an at least partially closeable aperture for the opening at the distal end of the housing, such that the loop comprises a plurality of elongated members, each of the plurality of elongated members extending between the one side of the loop and the opposite side of the loop, wherein each of the plurality of elongated members are extendable and closeable, using the actuation member, such that the opening is not obstructed by the plurality of elongated members of the loop in a first position of the capture tool and the at least partially closeable aperture is at least partially closed by the plurality of elongated members of the loop engaging the foreign body, while the opposite side of the loop remains attached to the housing, without changing the distance between the one side of the loop and the opposite side of the loop.

14. The retrieval system according to claim 13, wherein at least a portion of the capture tool is operatively connected to a cable disposed in a channel of the endoscope to facilitate remote operation of the capture tool, and wherein movement of the cable relative to the channel actuates the actuation member.

15. The retrieval system according to claim 13, wherein at least a portion of the actuation member is disposed within a sheath and is movable relative to the sheath, and wherein the sheath is disposed in a channel of the endoscope, and wherein movement of the actuation member relative to the sheath at least partially extends or retracts the loop such that the plurality of elongated members are extendable or closeable, respectively, when the loop is at least partially extended from the sheath or retracted into the sheath, respectively, while the opposite side of the loop remains attached to the housing.

16. The retrieval system of claim 15, wherein the actuation member is operatively connected to a remote operating device for moving the actuation member relative to the sheath, and wherein the loop is attached to the housing at a first attachment point, wherein the first attachment point comprises a first attachment member extending from an interior of the housing, and wherein the sheath is attached at a second attachment point configured to prohibit radial movement of the sheath relative to the housing.

17. The retrieval system of claim 16, wherein the first attachment member comprises a hook extending from an interior of the housing and the second attachment point comprises a second attachment member extending from the interior of the housing and configured to prohibit radial movement of the sheath relative to the housing.

18. A method of retrieving a foreign body from an esophagus of a patient using the foreign body retrieval device of claim 1, comprising:
    attaching the proximal end of the housing of the retrieval device of claim 1 to the distal end of an endoscope;
    coupling the actuation member to a portion of the housing;
    attaching the opposite side of the loop to a portion of the housing opposite of where the actuation member is coupled to the housing, such that the loop defines a plurality of elongated members forming the at least partially closeable aperture for the opening at the distal end of the housing;
    inserting a distal end of the endoscope into a patient's mouth;
    advancing the distal end of the endoscope and the retrieval device through the esophagus of the patient;
    receiving at least a portion of the foreign body in the at least one cavity of the housing;
    closing the at least partially closeable aperture by closing the plurality of elongated members, while the opposite side of the loop remains attached to the housing, without changing the distance between the one side of the loop and the opposite side of the loop, at least partially closing the at least partially closeable aperture, wherein the capture tool engages the foreign body; and
    removing the distal end of the endoscope and the retrieval device from the patient to retrieve the foreign body.

19. The method of claim 18, wherein the step of receiving includes suctioning at least the portion of the foreign body into the at least one cavity of the housing.

* * * * *